US007235237B2

(12) United States Patent
Loscalzo et al.

(10) Patent No.: US 7,235,237 B2
(45) Date of Patent: Jun. 26, 2007

(54) METHODS OF TREATING VASCULAR DISEASES CHARACTERIZED BY NITRIC OXIDE INSUFFICIENCY

(75) Inventors: Joseph Loscalzo, Dover, MA (US); Joseph A. Vita, Hingham, MA (US); Michael D. Loberg, Boston, MA (US); Manuel Worcel, Boston, MA (US)

(73) Assignee: NitroMed, Inc., Lexington, MA (US)

( * ) Notice: Subject to any disclaimer, the term of this patent is extended or adjusted under 35 U.S.C. 154(b) by 492 days.

(21) Appl. No.: 10/415,136

(22) PCT Filed: May 2, 2001

(86) PCT No.: PCT/US01/14245

§ 371 (c)(1),
(2), (4) Date: Apr. 25, 2003

(87) PCT Pub. No.: WO02/34303

PCT Pub. Date: May 2, 2002

(65) Prior Publication Data

US 2004/0005306 A1    Jan. 8, 2004

Related U.S. Application Data

(63) Continuation-in-part of application No. 09/697,317, filed on Oct. 27, 2000, now Pat. No. 6,635,273, and a continuation-in-part of application No. PCT/US00/29582, filed on Oct. 26, 2000.

(60) Provisional application No. 60/179,020, filed on Jan. 31, 2000, provisional application No. 60/162,230, filed on Oct. 29, 1999.

(51) Int. Cl.
*A61K 38/43* (2006.01)
*A61K 31/215* (2006.01)
*A01N 37/12* (2006.01)
*A01N 33/18* (2006.01)

(52) U.S. Cl. ............. 424/94.1; 514/509; 514/562; 514/676

(58) Field of Classification Search ............ 424/94.1, 424/94.4, 468; 514/18, 248, 458, 474, 509, 514/562, 683
See application file for complete search history.

(56) References Cited

U.S. PATENT DOCUMENTS

| 4,293,565 A | 10/1981 | Cordes et al. |
| 4,584,315 A | 4/1986 | Marshall |
| 4,868,179 A | 9/1989 | Cohn |
| 5,627,191 A | 5/1997 | Birch et al. |
| 5,645,839 A | 7/1997 | Chobanian et al. |
| 5,760,069 A | 6/1998 | Lukas-Laskey et al. |
| 5,891,459 A | 4/1999 | Cooke et al. |
| 5,902,821 A | 5/1999 | Lukas-Laskey et al. |
| 5,968,983 A | 10/1999 | Kaesemeyer |
| 5,973,011 A | 10/1999 | Noack et al. |
| 6,103,769 A | 8/2000 | Kelm |
| 6,117,872 A | 9/2000 | Maxwell et al. |
| 6,319,515 B1 | 11/2001 | Hidaka et al. |
| 6,458,797 B1 | 10/2002 | Adams et al. |
| 2004/0063719 A1 | 4/2004 | Adams et al. |

FOREIGN PATENT DOCUMENTS

| EP | 0327263 A | 8/1989 |
| EP | 0 968 713 A1 | 5/1998 |
| JP | 09059152 | 3/1997 |
| WO | WO 95/26725 | 10/1995 |
| WO | WO 98/21193 | 5/1998 |
| WO | WO 99/00361 | 1/1999 |
| WO | WO 99/66921 | 12/1999 |
| WO | WO 99/67231 | 12/1999 |
| WO | WO 01/35961 A | 5/2001 |

OTHER PUBLICATIONS

Dupuis, Cardiovascular Drugs and Therapy, 8(3):501-507 (1994).
Cohn et al, The New England Journal of Medicine, 325(5):303-310 (1991).
Cohn et al, The New England Journal of Medicine, 314(24):1547-1552 (1986).
Carson et al, Circulation, Supplement I, 92(8):I31-I32, Abstract No. 0145 (1995).
Francis et al, Circulation, Supplement VI, 87(6):VI40-VI48 (1993).
Pierpont et al, Chest, 73(1):8-13 (1978).
Massie et al, The American Journal of Cardiology, 40:794-801 (1977).

(Continued)

*Primary Examiner*—Jon Weber
*Assistant Examiner*—Kailash C. Srivastava
(74) *Attorney, Agent, or Firm*—Wilmer Cutler Pickering Hale and Dorr LLP

(57) ABSTRACT

The present invention provides methods of treating or preventing vascular diseases caused by nitric oxide (NO) insufficiency. The methods encompass administering a composition comprising an antioxidant, a compound to treat cardiovascular diseases, a nitrosated compound, a compound that donates, transfers or relases NO, or is a NO synthase substrate, or endogenously stimulates NO synthesis, or stimulates levels of endothelium derived relaxing factor. In the said composition, a hydralazine compound may be an antioxidant, isosorbide mono-or dinitrate may be the compound to donate, transfer, release, or stimulate endogenous NO synthesis. The isorsorbide may also elevate endogenous levels of endotherlium-derived relaxing factor, or be a NO synthase substrate and angiotensin enzyme inhibitor may be nitrosated compound. Disclosed in the invention is also a method to treat, or prevent Renaud's syndrome by administering a therapeutically effective amount of an antioxidant, a NO donor, a nitrosated compound and novel sustained-release formulations (e.g. a transdermal patch).

17 Claims, 3 Drawing Sheets

OTHER PUBLICATIONS

Kaplan et al, Annals of Internal Medicine, 84:639-645 (1976).
Bauer et al, Circulation, 84(1):35-39 (1991).
The SOLVD Investigators, The New England Journal of Medicine, 327(10):685-691 (1992).
Ziesche et al, Circulation, 87(6):VI56-VI64 (1993).
Rector et al, Circulation, 87(6):VI71-VI77 (1993).
Carson et al, Journal of Cardiac Failure, 5(3):178-187 (Sep. 10, 1999).
Dries et al, The New England Journal of Medicine, 340(8):609-616 (Feb. 25, 1999).
Freedman et al, Drugs, 54(Supp. 3):41-50 (1997).
Sherman et al, Cardiologia, 42(2):177-187 (1997).
Biegelson et al, Coronary Artery Disease, 10-241-256 (1999).
Rudd et al, Am. J. Physiol., 277(46):H723-H739 (1999).
Hammerman et al, Am. J. Physiol., 277(46):H1579-H1592 (1999).
Loscalzo et al, Transactions of the American and Climatological Ass., 111:158-163 (2000).
Johnson, Clinical Pharmacy, vol. 5, pp. 536 and 541 (1986).
Turner et al, The American Journal of Cardiology, 47:910-916 (1981).
Massie et al, Circulation, 63(3):658-664 (1981).
Nelson et al, Journal of Cardiovascular Pharmacology, 5(4):574-579 (1983).
Leier et al, Circulation, 63(1):102-109 (1981).
Wilson et al, The American Journal of Medicine, 71:627-633 (1981).
Biddle et al, J. Clin. Pharmacol., 21:343-350 (1981).
Margorien et al, Clinical Research, 27(4):A617 (1979), incomplete.
Turner et al, Clinical Research, 29(2):246A (1981), abstract only.
Hibiya et al, Japanese Circulation Journal, 45:966 (Abstract No. 338) (1981), abstract only.
Franciosa et al, Circulation, 59(6):1085-1091 (1979).
Lanas et al, Rev. Med. Chile, 107:926-930 (1979), abstract only.
Usdin et al, Coeur, 10(1):119-128 (1979), article in french only abstract considered.
Jun. 21, 2004. Supplementary Partial European Search Report for EP 00 97 6651.0.
Franciosa, Joseph A., "African-American Heart Failure Trial (A-HeFT): Rationale, Design, and Methodology," Journal of Cardiac Failure, vol. 8, No. 3, 2002, pp. 128-135.
Yancy, Clyde W., et al., "Race and the Response to Adrenergic Blockage with Carvedilol in Patients with Chronic Heart Failure," N. Engl. J. Med., vol. 344, No. 18, May 3, 2001, pp. 1358-1365.
Yancy, Clyde W., "Heart Failure in African Americans: A Cardiovascular Enigma," Journal of Cardiac Failure, vol. 6, No. 3, 2000, pp. 183-186.
Exner, Derek V., et al., "Lesser Response to Angiotensin-Converting-Enzyme Inhibitor Therapy in Black as Compared with White Patients with Left Ventricular Dysfunction," N. Engl. J. Med., vol. 344, No. 18, May 3, 2001, pp. 1351-1357.
Packer, Milton, et al., "Effect of Carvedilol on Survival in Severe Chronic Heart Failure," N. Engl. J. Med., vol. 344, No. 22, May 31, 2001, pp. 1651-1658.
"A Trial of the Beta-Blocker Bucindolol in Patients with Advanced Chronic Heart Failure," N. Engl. J. Med., vol. 344, No. 22, May 31, 2001, pp. 1659-1667.
Braunwald, Eugene, "Expanding Indications for Beta-Blockers in Heart Failure," N. Engl. J. Med., vol. 344, No. 22, May 31, 2001, pp. 1711-1712.
Schwartz, Robert S., "Racial Profiling in Medical Research," N. Engl. J. Med., vol. 344, No. 18, May 3, 2001, pp. 1392-1393.
Levine, T. Barry, "Paradoxical Hypertension after Reversal of Heart Failure in Patients Treated with Intensive Vasodilator Therapy," American Journal of Hypertension, Ltd., 1998; 11:1041-1047.
ABSTRACTS—Heart Failure 179A, JACC, Feb. 1999.
Kahn, Jonathan, "How a Drug Becomes "Ethnic": Law, Commerce, and the Production of Racial Categories in Medicine," Yale Journal of Heath Policy, Law, and Ethics IV:1 (2004), pp. 1-46.
Parker, John D., et al., "The Effect of Hydralazine on the Development of Tolerance to Continuous Nitroglycerin," The Journal of Pharmacology and Experimental Therapeutics, vol. 280, No. 2, pp. 866-875.
Kalinowski, Leszek, et al., "Race-Specific Differences in Endothelial Function—Predisposition of African Americans to Vascular Diseases," Circulation, Jun. 1, 2004, pp. 2511-2517.
Tucker, A. T. et al. Nov. 13, 1999, "Effect of nitric-oxide-generating system on microcirculatory blood flow in skin of patients with severe Raynaud's syndrome: a randomised trial", lancet vol. 354, #13, pp. 1670-1675.
Apr. 05, 2005. Supplementary European Search Report from European Patent Application No. 01932915.0.
Burnier et al, Hypertension, 22(3):339-347 (Sep. 1993), recieved May 30, 2006.
von Lutterotti et al, American Journal of Hypertension, 4(4 Part 2):346S-349S (1991), recd May 30, 2006.
Massie et al, Br. Heart J., 45:376-384 (1981), recd. May 30, 2006.
Lanas et al, Rev. Med. Chile, 107:926-930 (1979).
Usdin et al, Coeur, 10(1):119-128 (1979).
Parker, John D., et al., "The Effect of Hydralazine on the Development of Tolerance to Continuous Nitroglycerin," The Journal of Pharmacology and Experimental Therapeutics, vol. 280, No. 2, pp. 866-875, 1997.

METHODS OF TREATING VASCULAR DISEASES CHARACTERIZED BY NITRIC OXIDE INSUFFICIENCY

RELATED APPLICATIONS

This application is a continuation-in-part of U.S. application Ser. No. 09/697,317, filed Oct. 27, 2000 now U.S. Pat. No. 6,635,273, and PCT Application No. PCT/US00/29582, filed Oct. 26, 2000, both of which claim priority to U.S. Provisional Application No. 60/162,230 filed Oct. 29, 1999 and U.S. Provisional Application No. 60/179,020 filed Jan. 31, 2000.

FIELD OF THE INVENTION

The present invention provides methods of treating and/or preventing vascular diseases characterized by nitric oxide insufficiency by administering a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. The antioxidant may preferably be a hydralazine compound or a pharmaceutically acceptable salt thereof. The compound that donates, transfers or releases nitric oxide, elevates endogenous levels of endothelium-derived relaxing factor, stimulates endogenous synthesis of nitric oxide or is a substrate for nitric oxide synthase may preferably be isosorbide dinitrate and/or isosorbide mononitrate. The present invention also provides methods of treating and/or preventing vascular diseases characterized by nitric oxide insufficiency by administering a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases. The present invention also provides methods of treating and/or preventing Raynaud's syndrome by administering a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated calcium channel blocker, nitrosated endothelin antagonist, nitrosated angiotensin II receptor antagonist and/or nitrosated renin inhibitor. The present invention also provides novel transdermal patches comprising at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. The present invention also provides sustained release formulation comprising at least one antioxidant or a pharmaceutically acceptable salt thereof, and at least one nitric oxide donor, and, optionally, at least one nitrosated compound.

BACKGROUND OF THE INVENTION

The decline in cardiovascular morbidity and mortality in the United States over the past three decades has been the result of significant advances in research on cardiovascular disease mechanisms and therapeutic strategies. The incidence and prevalence of myocardial infarction and death from myocardial infarction, as well as that from cerebrovascular accident, have decreased significantly over this period largely owing to advances in prevention, early diagnosis, and treatment of these very common diseases.

Analysis of outcomes by race, however, paints quite a different picture: life expectancy and cardiovascular morbidity rates have improved far less for blacks than whites. Available data show that the likelihood of dying from cardiovascular disease is far greater among black Americans than among white Americans. In this decade, the death rate from cardiovascular disease for black males was 353 per 100,000 population, while that for white males was 244 per 100,000; the rate for black females was 226 per 100,000; while that for white females was 135 per 100,000. Consonant with this important demographic parameter is the observation that there is a higher prevalence of several of the important risk factors for cardiovascular disease, e.g., hypertension, smoking, diabetes mellitus, obesity, and left ventricular hypertrophy, among blacks compared with whites. In addition, outcomes of cardiovascular events are worse for blacks than whites. Following myocardial infarction, blacks have a 50% higher annual mortality rate than whites, and their five year survival is only 70%. Thus, the many advances in cardiovascular medicine that account for the overall improvement in cardiovascular health in the general population have failed to translate into comparable racial benefits.

There is a need in the art for new and more effective compositions and methods for treating vascular diseases. The present invention is directed to these, as well as other, important ends.

SUMMARY OF THE INVENTION

The present invention provides methods for treating and/or preventing vascular diseases characterized by nitric oxide insufficiency by administering to a patient a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. The antioxidant may preferably be a hydralazine compound or a pharmaceutically acceptable salt thereof. The compound that donates, transfers or releases nitric oxide, elevates endogenous levels of endothelium-derived relaxing factor, stimulates endogenous synthesis of nitric oxide or is a substrate for nitric oxide synthase may preferably be isosorbide dinitrate and/or isosorbide mononitrate. The antioxidant and the nitric oxide donor and optional nitrosated compound and/or compound used to treat cardiovascular diseases can be administered separately or as components of the same composition.

Another aspect of the present invention provides methods for treating and/or preventing vascular diseases characterized by nitric oxide insufficiency by administering to a patient a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases. The nitrosated compound and optional antioxidant and/or compound used to treat cardiovascular diseases can be administered separately or as components of the same composition.

In another aspect, the present invention provides methods for treating and/or preventing Raynaud's syndrome by administering to a patient a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated calcium channel blocker, nitrosated endothelin antagonist, nitrosated angiotensin II receptor antagonist and/or nitrosated renin inhibitor. The antioxidant, nitric oxide donor, and nitrosated compound can be administered separately or as components of the same composition.

In yet another aspect, the present invention provides novel transdermal patches comprising a therapeutically effective amount of at least one antioxidant at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases.

In another aspect, the present invention provides sustained release formulations comprising a therapeutically effective amount of at least one antioxidant or a pharmaceutically acceptable salt thereof, and at least one nitric oxide donor, and, optionally, at least one nitrosated compound.

These and other aspects of the present invention are described in more detail herein.

BRIEF DESCRIPTION OF THE FIGURES

FIG. 2 shows that endothelium-derived NO action is impaired in the forearm microvessels of the black patients compared to the white patients.

DETAILED DESCRIPTION OF THE INVENTION

Figure 1:
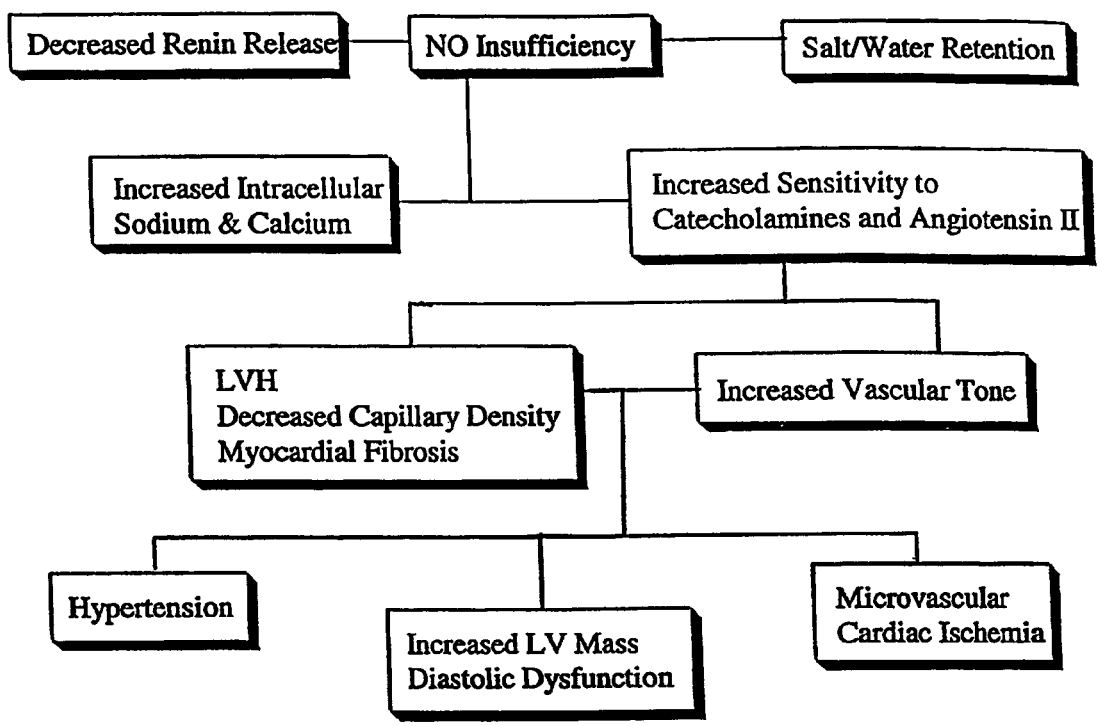
FIG. 1 shows that nitric oxide (NO) insufficiency is associated with increased salt and water retention and a low-renin state. Increased intracellular sodium and calcium in conjunction with reduced NO leads to enhanced sensitivity of vascular smooth muscle cells and cardiomyocytes to the tonic and growth-stimulating properties of catecholamines and angiotensin II. Increased vascular tone, left ventricular hypertrophy with inadequate capillary angiogenesis, and increased matrix production with myocardial fibrosis result. These intermediate phenotypes lead to the clinical disorders of low-renin, salt-sensitive hypertension; disproportionate left ventricular hypertrophy and diastolic dysfunction; and microvascular myocardial ischemia.

As used throughout the disclosure, the following terms, unless otherwise indicated, shall be understood to have the following meanings.

"Patient" refers to animals, preferably mammals, most preferably humans, and includes males and females.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of a therapeutically active compound and/or composition such that the blood levels of the therapeutically active compound are maintained within a desirable therapeutic range over an extended period of time. The sustained release formulation can be prepared using any conventional method known to one skilled in the art to obtain the desired release characteristics.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\cdot$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO-$, $NO\cdot$), such that the biological activity of the nitrogen monoxide species is expressed at the intended site of action.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkylnyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0]octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro.

Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated, unsaturated, cyclic or aromatic or polycyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon-carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Aryloxy" refers to $R_{55}O$—, wherein $R_{55}$ is an aryl group, as defined herein. Exemplary aryloxy groups include napthyloxy, quinolyloxy, isoquinolizinyloxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O$^-$R$_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{50}R_{52}N$—, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" refers to $R_{50}R_{55}N$—, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2$$^-$.

"Sulfonic acid" refers to —S(O)$_2$OR$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an arylheterocyclic ring, as defined herein, or $R_{51}$ and $R_{57}$ taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein.

"Arylthio" refers to $R_{55}S$—, wherein $R_{55}$ is an aryl group, as defined herein.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O—$ wherein $R_{51}$ is a hydrogen atom, an alkyl group, an aryl group, an alkylaryl group, or an arylheterocyclic ring, as defined herein.

"Carbamoyl" refers to $—O—C(O)N(R_{51})(R_{57})$, wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cycloalkyl group, as defined herein.

"Carbamate" refers to $R_{51}O—C(O)N—(R_{57})$, wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to $—C(O)OR_{76}$, wherein $R_{76}$ is a hydrogen, an organic cation or an inorganic cation, as defined herein.

"Carbonyl" refers to $—C(O)—$.

"Alkylcarbonyl" or "alkanoyl" refers to $R_{50}—C(O)—$, wherein $R_{50}$ is an alkyl group, as defined herein.

"Arylcarbonyl" or "aroyl" refers to $R_{55}—C(O)—$, wherein $R_{55}$ is an aryl group, as defined herein.

"Carboxylic ester" refers to $—C(O)OR_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to $—C(O)N(R_{51})(R_{57})$, wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to $—N(R_{59})—C(O)N(R_{51})(R_{57})$ wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together with the nitrogen to which they are attached form a heterocyclic ring, as defined herein.

"Phosphoryl" refers to $—P(R_{70})(R_{71})(R_{72})$, wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

"Silyl" refers to $—Si(R_{73})(R_{74})(R_{75})$, wherein $R_{73}$, $R_{74}$ and $R_{75}$ are each independently a covalent bond, a lower alkyl, an alkoxy, an aryl or an arylalkoxy, as defined herein.

"Hydrazino" refers to $H_2N—N(H)—$.

"Hydralazine compound" refers to a compound having the formula:

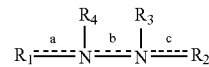

wherein a, b and c are independently a single or double bond; $R_1$ and $R_2$ are each independently a hydrogen, an alkyl, an ester or a heterocyclic ring, wherein alkyl, ester and heterocyclic rind are as defined herein; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like.

"Compound used to treat cardiovascular diseases" refers to any therapeutic compound, or a pharmaceutically acceptable salt thereof, used to treat any cardiovascular disease. Suitable compounds include, but are not limited to, angiotensin-converting enzyme (ACE) inhibitors (such as, for example, alacepril, benazepril, captopril, ceronapril, cilazapril, delapril, duinapril, enalapril, enalaprilat, fosinopril, imidapril, lisinopril, losartan, moveltipril, naphthopidil, pentopril, perindopril, quinapril, ramipril, rentipril, spirapril, temocapril, trandolapril, urapidil, zofenopril, and the like); beta-adrenergic blockers (such as, for example, acebutolol, alprenolol, amosulalol, arotinolol, atenolol, betaxolol, bethanidine, bevantolol, bisoprolol, bopindolol, bucumolol, bufetolol, bufuralol, bunitrolol, bupranolol, butafilolol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, and the like); cholesterol reducers (such as, for example, HMG-CoA reductase inhibitors, including, but not limited to, lovastatin (MEVACOR®), simvastatin (ZOCOR®), pravastatin (PRAVACHOL®), fluvastatin, cerivastatin (BAYCOL®), atorvastatin (LIPITOR®), and the like; sequestrants, including, but not limited to, cholestyramine, colestipol, sialkylaminoalkyl derivatives of cross-linked dextran, and the like; inhibitors of cholesterol absorption, including, but not limited to, beta-sitosterol, acyl CoA-cholersterol acyltransferase inhibitors, melinamide, and the like); calcium channel blockers (such as, for example, amlodipine, aranidipine, barnidipine, benidipine, cilnidipine, clentiazem, diltiazem, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like); angiotensin II receptor antagonists (such as, for example, ciclosidomine, eprosartan, furosemide, irbesartan, losartan, saralasin, valsartan, and the like); endothelin antagonists (such as, for example, bosentan, sulfonamide endothelin antagonists, BQ-123, SQ 28608, and the like); renin inhibitors (such as, for example, enalkrein, RO 42–5892, A 65317, CP 80794, ES 1005, ES 8891, SQ 34017, and the like); and mixtures thereof.

"Vascular diseases characterized by nitric oxide insufficiency" include, but are not limited to, cardiovascular diseases; diseases resulting from oxidative stress; hypertension (e.g., low-renin hypertension; salt-sensitive hypertension; low-renin, salt-sensitive hypertension; primary pulmonary hypertension; thromboembolic pulmonary hypertension; pregnancy-induced hypertension; renovascular hypertension; hypertension-dependent end-stage renal disease), heart failure (e.g., microvascular cardiac ischemia), and left ventricular hypertrophy with disproportionate microvascularization, (i.e., inadequate vascularity) or diastolic dysfunction.

"Cardiovascular diseases" refers to any cardiovascular disease, including but not limited to, congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, cardiac edema, renal insufficiency, nephrotic edema, hepatic edema, stroke, transient ischemic attacks, cerebrovascular accidents, restenosis, controlling blood pressure in hypertension, platelet adhesion, platelet aggregation, smooth muscle cell proliferation, vascular complications associated with the use of medical devices, wounds associated with the use of medical devices, pulmonary thromboembolism, cerebral thromboembolism, thrombophlebitis, thrombocytopenia, bleeding disorders, and the like.

"Diseases resulting from oxidative stress" refers to any disease that involves the generation of free radicals or radical compounds, such as, for example, atherogenesis, atheromatosis, arteriosclerosis, artherosclerosis, vascular hypertrophy associated with hypertension, hyperlipoproteinaemia, normal vascular degeneration through aging, parathyroidal reactive hyperplasia, chronic renal disease, neoplastic diseases, inflammatory diseases, neurological and acute bronchopulmonary disease, tumorigenesis, ischemia-reperfusion syndrome, arthritis, sepsis, and the like.

Two broad classes of cardiovascular disorders are more prevalent among blacks than whites and serve as areas in need of investigative efforts. Hypertension and left ventricular hypertrophy, two related yet independent risk factors for coronary heart disease, are significantly more prevalent among blacks than whites. Blacks also have higher rates of angiographically normal coronary arteries despite a higher prevalence of risk factors for coronary atherosclerosis, and greater morbidity and mortality from coronary heart disease than whites. These paradoxical observations have led some investigators to postulate that blacks harbor a diathesis of the microvasculature that limits perfusion and serves as a stimulus for vascular smooth muscle cell and cardiomyocyte hypertrophy, which, in turn, leads to hypertension and left ventricular hypertrophy, respectively. The underlying basis for this vascular diathesis may involve the endothelium, which has a limited capacity to generate vasodilator and antiproliferative factors or an increased capacity to produce vasoconstrictor and proliferative factors; the vascular smooth muscle cell, which manifests increased sensitivity to vasoconstrictor and proliferative factors; or both, in these individuals.

The present inventors have discovered that a major product of the normal blood vessel that may play a role in the vascular diathesis of blacks is endothelium-derived nitric oxide (NO). Nitric oxide produced by the endothelial cells induces vascular smooth muscle cell relaxation, contributing importantly to resting vascular tone. In addition, NO inhibits vascular smooth muscle cell proliferation and induces apoptosis in smooth muscle cells, which leads to the release of basic fibroblast growth factor and vascular endothelial cell growth factor, in turn supporting endothelial cell proliferation. This sequence of cellular responses is believed to sustain angiogenesis under hypoxic or ischemic conditions.

The role of nitric oxide in the vascular diathesis of blacks is illustrated by the consequences of nitric oxide insufficiency in the normal responses of the vasculature to nitric oxide. Nitric oxide insufficiency suppresses renin release from the juxtaglomerular cells, and induces a sodium chloride/volume sensitive increase in blood pressure. Furthermore, nitric oxide insufficiency leads to an increased sensitivity of vascular smooth muscle cells to vasoconstrictors, such as angiotensin II and catecholamines, which amplify the increase in vascular resistance.

Nitric oxide insufficiency promotes vascular smooth muscle cell proliferation following vascular injury, and sustains smooth muscle cell and cardiomyocyte hypertrophy in response to catecholamines and angiotensin II. Furthermore, inadequate nitric oxide leads to increased production of extracellular matrix with consequent myocardial fibrosis.

These many cardiovascular responses that result from inadequate NO in the vasculature have clear clinical correlates in the black population. The clinical vascular phenotype of blacks that distinguishes them from whites with similar cardiovascular disorders is one of salt-sensitive, low-renin hypertension; left ventricular hypertrophy disproportionate to afterload and with an inadequate angiogenic response; and microvascular ischemia in the absence of significant epicardial coronary artery disease. The net pathophysiological consequences of these effects are increased peripheral vascular resistance with accompanying arterial hypertension; and an inadequately vascularized, fibrotic increase in left ventricular mass with accompanying diastolic dysfunction and microvascular ischemia.

Given these clinical observations and the role that NO plays in preventing their development, the present inventors have unexpectedly discovered that the principal cardiovascular disorders common among blacks (such as hypertension, left ventricular hypertrophy, and heart failure) result from a specific vascular diathesis that is a direct consequence of nitric oxide insufficiency. An outline of the pathogenic consequences of nitric oxide insufficiency that serve as the basis for these cardiovascular disorders is shown in FIG. 1.

Nitric oxide insufficiency states can be a consequence of reduced synthesis of nitric oxide, enhanced inactivation of nitric oxide, or both. Possible candidate mechanisms include alterations in the genes that code for endothelial nitric oxide synthase or the inducible microvascular and cardiomyocyte nitric oxide synthase leading to reduced expression of a normal gene product or appropriate expression of a less active gene product; reduction in the enzymatic activity of nitric oxide synthase owing to inadequate cofactor concentrations; or enhanced inactivation of nitric oxide by oxidant stress.

Data obtained by the inventors in cultured cells, animal models, and human patients suggest that increased oxidant stress is central to the vascular diathesis of and consequent cardiovascular disorders common among African Americans. Possible candidate mechanisms for the oxidant stress include enhanced production of reactive oxygen species (ROS), decreased antioxidant defenses, or both. The inventors make no a priori assumptions about the temporal or causative relationship between oxidant stress and the vascular phenotype of blacks: oxidant stress may both precede the development of the vascular diathesis and promote its progression once established. Recent data suggest that enhanced ROS production accompanies essential hypertension, atherosclerosis, thrombosis, and diabetes mellitus, and appears in each case, at the very least, to be important in the progression of established disease, if not in its actual genesis.

Endothelium-derived relaxing factor (EDRF), first described by Furchgott et al, *Nature*, 299:373–376 (1980), is an important mediator of vascular function. This endothelial product activates guanylyl cyclase in vascular smooth muscle cells and platelets, leading to vasorelaxation and platelet inhibition, respectively (Loscalzo et al, *Prog Cardiovasc Dis*, 38:87–104 (1995)). The chemical nature of EDRF has been studied using a variety of pharmacological and analytical techniques, and is NO (Ignarro et al, *Circ Res*, 61:866–879 (1987); Palmer et al, *Nature*, 327:524–526 (1987)).

Nitric oxide is synthesized by one of several isoforms of the NO synthase (NOS) family of enzymes, two of which are found in the vasculature, endothelial NOS (eNOS) and inducible NOS (iNOS). eNOS is synthesized by endothelial cells, while iNOS is synthesized by a variety of cell types, including vascular smooth muscle cells, fibroblasts, and (principally microvascular) endothelial cells (Balligand et al, *Am J Physiol*, 268:H1293–1303 (1995)). These enzymes produce NO as a result of the five-electron oxidation of L-arginine to L-citrulline; requisite cofactors include calcium-calmodulin, $O_2$, FAD, FMN, tetrahydrobiopterin thiols, heme, and NADPH. (Moncada et al, *N Engl J Med*, 329:2002–2012 (1993)).

The role of NO in the cardiovascular system has become increasingly apparent over the past fifteen years (Loscalzo et al, *Prog Cardiovasc Dis*, 38:87–104 (1995)). Nitric oxide contributes importantly to resting tone in conductance as well as resistance arteries (Ouyyumi et al, *J Clin Invest*, 95:1747–1755 (1995)), and plays a critical role in the maintenance of peripheral vascular resistance and arterial pressure responses. Inhibition of NOS activity is associated with enhanced vascular sensitivity to vasoconstrictors, such as norepinephrine and angiotensin II (Conrad et al, *Am J Physiol*, 262:R1137-R1144 (1992)), and this effect appears to be mediated, in part, by increased calcium sensitivity (Bank et al, *Hypertension*, 24:322–328 (1994)). Nitric oxide release from the cardiovascular regulatory center in the brain may also be involved in the central regulation of blood pressure, suggesting a role for neuronal NOS in the regulation of vascular tone (Cabrera et al, *Biochem Biophys Res Comm*, 206:77–81 (1995); Mattson et al, *Hypertension*, 28:297–303 (1996)).

Nitric oxide activates renin gene expression in the kidney, and is involved in the baroreceptor-mediated regulation of renin gene expression (Schricker et al, *Pflug Arch*, 428:261–268 (1994)). The dependence of blood pressure on salt intake appears to depend on NO, and NO deficiency states are associated with salt-sensitivity (Tolins et al, *Kidney Internat*, 46:230–236 (1994)). Selective inhibition of iNOS in Dahl R rats has been shown to lead to salt-sensitivity and to the development of salt-dependent hypertension similar to Dahl S rats (Rudd et al, *Am J Physiol*, 277: H732–H739 (1999)). In addition, mice deficient in iNOS (iNOS gene eliminated by targeted disruption) may develop hypertension in response to salt feeding (Rudd et al, *Circulation*, 98:1A (1998)).

Nitric oxide also affects myocardial contractility, and does so both by mediating muscarinic-cholinergic slowing of the heart rate and the contractile response to beta-adrenergic stimulation (Balligand et al, *Proc Nat'l Acad Sci USA*, 90:347–351 (1993)). This latter effect appears to be mediated in vivo through the vagus nerve (Hare et al, *J Clin Invest*, 95:360–366 (1995)).

In both vascular smooth muscle cells and cardiomyocytes, NO inhibits cellular proliferation and limits the proliferative response to growth-promoting substances (Garg et al, *J Clin Invest*, 83:1774–1777 (1986)). Left ventricular hypertrophy tends to occur in adult hearts with inadequate capillary proliferation, and this may account for the microvascular ischemia noted in patients with hypertrophy. Capillary proliferation is generally held to be a rare event in normal adult mammalian hearts. However, recent data from a hypertensive rat model, in which left ventricular hypertrophy commonly occurs, show that treatment with a low-dose of an angiotensin-converting enzyme inhibitor insufficient to prevent hypertension and left ventricular hypertrophy can, nonetheless, evoke capillary angiogenesis. Compared with untreated controls, treatment with the angiotensin converting enzyme inhibitor increased myocardial capillary proliferation (Unger et al, *Hypertension*, 20:478482 (1992)), and this effect was believed to be a consequence of inhibiting the degradation and potentiating the action of bradykinin. Bradykinin increases myocardial blood flow by inducing release of NO from microvascular endothelial cells, and increased blood flow is a powerful stimulus for capillary proliferation (Mall et al, *Bas Res Cardiol*, 85:531–540 (1990)).

Normal metabolic processes in vascular cells are associated with the generation of reactive oxygen intermediates that must be neutralized to limit oxidative damage and cellular dysfunction. In the setting of common cardiovascular disorders or in the presence of common risk factors for atherothrombotic disease, reactive oxygen species (ROS) are generated in abundance, and their rate of synthesis and flux typically exceeds the capacity of endogenous antioxidant mechanisms. Hypercholesterolemia, hyperglycemia (Keaney et al, *Circulation*, 99:189–191 (1999)), cigarette smoking, hyperhomocysteinemia, hypertension, and frank atherosclerosis are all accompanied by an increase in plasma and tissue ROS generation. Superoxide anion, hydrogen peroxide, hydroxyl radical, peroxynitrite, and lipid peroxides all increase in these settings. What remains unknown is whether or not the increase in ROS in these disorder is a primary event, a secondary consequence of the underlying process, or both.

Endogenous antioxidants important for the neutralization (i.e., reduction) of ROS can be categorized into two groups: small-molecule antioxidants and antioxidant enzymes. The former group comprises molecules such as GSH, NADPH, α-tocopherol, vitamin C, and ubiquinol-10; while the latter group comprises the superoxide dismutases, catalase, and glutathione peroxidases. Deficiencies in several of these molecular species have been shown to lead to increased steady-state levels of ROS and vascular dysfunction, including increased platelet activation, arterial thrombosis (Freedman et al, *J Clin Invest*, 97:979–987 (1996); Freedman et al, *Circulation*, 98:1481–1486 (1998)), and reduced production of platelet-derived NO (Kenet et al, *Arterio Thromb Vasc Biol*, 19(8): 2017–2023 (1999)), which is important for limiting expansion of a platelet thrombus (Freedman et al, *Circ Res*, 84:1416–142 (1999)).

ROS generation accompanies the vascular dysfunction associated with several models of atherothrombotic and hypertensive vascular diseases. Hyperhomo-cysteinemic mice (i.e., cystathionine β-synthase knock-out mice) (Eberhardt et al, *Circulation*, 98:144 (1998)), cellular glutathione peroxidase-deficient mice (i.e., cellular glutathione peroxidase knock-out mice), and salt-induced hypertensive rats (i.e., salt-fed Dahl S rats) (Trolliet et al, *Circulation*, 98:1–725 (1998)) all manifest increased vascular ROS, and this increase in ROS is accompanied by reduced NO bioactivity through oxidative inactivation. Endothelial function and NO availability can be improved by improving antioxidant status with a cysteine precursor (Vita et al, *J Clin Invest,* 101:1408–1414 (1998)). In addition, α-tocopherol leads to platelet inhibition (Freedman et al, *Circulation,* 94:2434–2440 (1996)) as one mechanism of its atherothrombotic benefit (Stephens et al, Lancet, 347:781–786 (1996)). The present inventors have also discovered that salt-loading salt-sensitive individuals (Dahl S rats) leads to an approximate 5-fold increase in plasma $F_2$-isoprostanes (8-epi-prostaglandin $F_2$), and this increase precedes the development of florid hypertension. These data all support the role of oxidant stress in the genesis or evolution of vascular dysfunction and disease, and the importance of antioxidant mechanisms in preventing this pathobiology, particularly with regard to African Americans.

In support of the mechanisms illustrated above, minimum forearm vascular resistance is significantly higher among normotensive blacks than whites (Bassett et al, *Am J Hypertension,* 5:781–786 (1992)), and forearm blood-flow responses to isoproterenol are markedly attenuated in normotensive blacks, suggesting a blunted $\beta_2$-vasodilator response in these individuals (Lang et al, *N Engl J Med,* 333:155–160 (1995)). Blacks tend to have greater left ventricular mass than whites for any given level of blood pressure (Koren et al, *Am J Hypertension,* 6:815–823 (1993); Chaturvedi et al, *J Am Coll Cardiol,* 24:1499–1505 (1994)). While not quantitated in any necropsy study, this response is likely to be accompanied by inadequate capillary angiogenesis which, in turn, may account for the diastolic dysfunction and the microvascular ischemia observed in blacks. Interestingly, blacks have been observed to have low levels of urinary kallikrein (Zinner et al, *Am J Epidemiol,* 104:124–132 (1976); Levy et al, *J Clin Invest,* 60:129–138 (1977)), the enzyme responsible for the generation of bradykinin from high-molecular-weight kininogen. Thus, were a similar abnormality in bradykinin and bradykinin-mediated NO production to exist in the coronary vasculature, attenuated blood flow responses may result that would limit capillary angiogenic responses and prevent the endothelial proliferative effects of locally derived NO.

As discovered and described herein, African Americans have a unique vascular diathesis that may serve as the basis for clinically important cardiovascular syndromes. For example, differences in the outcome of left ventricular dysfunction may be a consequence of the enhanced (perhaps salt-dependent) increase in oxidant stress coupled with microvascular endothelial dysfunction and an inadequately vascularized, hypertrophied left ventricle. This constellation of pathophysiological abnormalities may provide the substrate for the important differences in outcome between blacks and whites with left ventricular dysfunction (Dreis et al, *N Engl J Med,* 340:609–616 (1999)). In addition, these observations and their clinical consequences suggest that blacks with abnormal endothelial function and nitric oxide insufficiency states would derive direct and, perhaps, disproportionate clinical benefit from enhancing nitric oxide in the vasculature, either by improving endothelial function, providing exogenous nitric oxide donors, or both.

In view of the above, the present invention provides methods of treating and/or preventing vascular diseases characterized by nitric oxide (NO) insufficiency by administering a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases. For example, the patient can be administered an antioxidant and a nitric oxide donor, or the patient can be administered an antioxidant, a nitric oxide donor and a nitrosated compound, or the patient can be administered an antioxidant, a nitric oxide donor, a nitrosated compound and a compound used to treat cardiovascular diseases.

Another aspect of the present invention provides methods for treating and/or preventing vascular diseases characterized by nitric oxide insufficiency by administering to a patient a therapeutically effective amount of at least one nitrosated angiotensin-converting enzyme inhibitor, nitrosated beta-adrenergic blocker, nitrosated calcium channel blocker, nitrosated endothelin antagonist, nitrosated angiotensin II receptor antagonist and/or nitrosated renin inhibitor, and, optionally, at least one antioxidant and/or at least one compound used to treat cardiovascular diseases.

The present invention also provides methods of preventing and treating Raynaud's syndrome by administering a therapeutically effective amount of at least one antioxidant or a pharmaceutically acceptable salt thereof, and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated calcium channel blocker, nitrosated endothelin antagonist, nitrosated angiotensin II receptor antagonist and/or nitrosated renin inhibitor. For example, the patient can be administered an antioxidant and a nitric oxide donor, or the patient can be administered an antioxidant and a nitrosated compound. The antioxidant, nitric oxide donor and nitrosated compound can be administered separately or as components of the same composition. Raynaud's syndrome is a condition that causes a loss of blood flow to the fingers, toes, nose and/or ears. The affected area turns white from the lack of circulation, then blue and cold, and finally numb. The affected area may also turn red, and may throb, tingle or swell.

Another aspect of the present invention provides novel transdermal patches comprising a therapeutically effective amount of at least one antioxidant and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, and/or at least one compound used to treat cardiovascular diseases Yet another aspect of the present invention provides sustained release formulations comprising a therapeutically effective amount of at least one antioxidant or a pharmaceutically acceptable salt thereof, and at least one nitric oxide donor, and, optionally at least one nitrosated compound.

In the present invention, the antioxidants include small-molecule antioxidants and antioxidant enzymes. Antioxidant refers to and includes any compound that can react and quench a free radical. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, and the like. Suitable antioxidant enzymes include, but are not limited to, superoxide dismutase, catalase, glutathione peroxidase, and the like. The antioxidant enzymes can be delivered by gene therapy as a viral vertor and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file reg.

The preferred antioxidant may be a hydralazine compound that might preferably be administered as a pharmaceutically acceptable salt; more preferably as hydralazine hydrochloride. Hydralazine hydrochloride (1-hydrazinophthalazine monohydrochloride), USP, is a white to off-white crystalline powder. It is soluble in water, slightly soluble in ethanol and practically insoluble in ether. Hydralazine hydrochloride is commercially available from, for example, Lederle Standard Products (Pearl River, N.Y.), and Par Pharmaceuticals Inc. (Spring Valley, N.Y.).

Compounds contemplated for use in the present invention (e.g., antioxidants) are used in combination with nitric oxide and compounds that release nitric oxide or otherwise directly or indirectly deliver or transfer nitric oxide to a site of its activity, such as on a cell membrane in vivo.

Nitrogen monoxide can exist in three forms: NO– (nitroxyl), NO. (nitric oxide) and NO$^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO$^+$) does not react with $O_2$ or $O_2$— species, and functionalities capable of transferring and/or releasing NO$^+$ and NO– are also resistant to decomposition in the presence of many redox metals. Consequently, administration of charged NO equivalents (positive and/or negative) does not result in the generation of toxic by-products or the elimination of the active NO moiety.

The term "nitric oxide" encompasses uncharged nitric oxide (NO.) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitric oxide releasing, delivering or transferring compounds, have the structure F—NO, wherein F is a nitric oxide releasing, delivering or transferring moiety, include any and all such compounds which provide nitric oxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-((E)-hydroxyimino)-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetyl-penicillamine, S-nitroso-homocysteine, S-nitroso-cysteine, S-nitroso-glutathione and S-nitroso-cysteinyl-glycine.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) HS(C($R_e$)($R_f$))$_m$SNO;

(ii) ONS(C($R_e$)($R_f$))$_m$$R_e$; and (iii) $H_2N$—CH($CO_2H$)—($CH_2$)$_m$—C(O)NH—CH($CH_2$SNO)—C(O)NH—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, -T-Q, or (C($R_e$)($R_f$))$_k$-T-Q, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)(R$_e$)(R$_f$), or —(N$_2$O$_2$—)$^-$.M$^+$, wherein M$^+$ is an organic or inorganic cation; with the proviso that when R$_i$ is —CH$_2$—C(T-Q)(R$_e$)(R$_f$) or —(N$_2$O$_2$—).M$^+$; then "—T-Q" can be a hydrogen, an alkyl group, an alkoxyalkyl group, an aminoalkyl group, a hydroxy group or an aryl group.

In cases where R$_e$ and R$_f$ are a heterocyclic ring or R$_e$ and R$_f$ when taken together with the carbon atoms to which they are attached are a heterocyclic ring, then R$_i$ can be a substituent on any disubstituted nitrogen contained within the radical wherein R$_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one O$_2$N—O—, O$_2$N—N—, O$_2$N—S— or O$_2$N—C— group. Preferred among these compounds are O$_2$N—O—, O$_2$N—N—, O$_2$N—S— or O$_2$N—C— polypeptides (the term "polypeptide" includes proteins and also polyamino acids that do not possess an ascertained biological function, and derivatives thereof); O$_2$N—O—, O$_2$N—N—, O$_2$N—S— or O$_2$N—C-amino acids (including natural and synthetic amino acids and their stereoisomers and racemic mixtures); O$_2$N—O—, O$_2$N—N—, O$_2$N—S— or O$_2$N—C-sugars; O$_2$N—O—, O$_2$N—N—, O$_2$N—S— or O$_2$N—C— modified and unmodified oligonucleotides (comprising at least 5 nucleotides, preferably 5–200 nucleotides); O$_2$N—O—, O$_2$N—N—, O$_2$N—S— or O$_2$N—C— straight or branched, saturated or unsaturated, aliphatic or aromatic, substituted or unsubstituted hydrocarbons; and O$_2$N—O—, O$_2$N—N—, O$_2$N—S— or O$_2$N—C— heterocyclic compounds. Preferred examples of compounds comprising at least one O$_2$N—O—, O$_2$N—N—, O$_2$N—S— or O$_2$N—C— group include isosorbide dinitrate, mononitrate, clonitrate, erythrityl tetranitrate, mannitol hexanitrate, nitroglycerin, pentaerythritoltetranitrate, pentrinitrol and propatylnitrate, most preferred are isosorbide dinitrate and/or isosorbide mononitrate.

Another group of NO adducts are N-oxo-N-nitrosoamines that donate, transfer or release nitric oxide and are represented by the formula: R$^1$R$^2$—N(O—M$^+$)—NO, where R$^1$ and R$^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and M$^+$ is as defined herein.

Another group of NO adducts are thionitrates that donate, transfer or release nitric oxide and are represented by the formula: R$^1$—(S)—NO$_2$, where R$^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where R$^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO−) and uncharged nitric oxide (NO.).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524–526 (1987); Ignarro et al, *Proc. Natl. Acad. Sci. USA,* 84:9265–9269 (1987)).

In the present invention the compound that donates, transfers or releases nitric oxide as a charged species, or elevates levels of endogenous EDRF or nitric oxide, or is a substrate for nitric oxide synthase may preferably be isosorbide dinitrate and/or isosorbide mononitrate, more preferably isosorbide dinitrate. Diluted isosorbide dinitrate (1,4, 3,6-dianhydro-D-glucitol-2,5-dinitrate), USP, is a white to off-white powder that has a melting point of 70° C. and has an optical rotation of +135° (3 mg/mL, ethanol). It is freely soluble in organic solvents such as ethanol, ether and chloroform, but is sparingly soluble in water. Isosorbide dinitrate is commercially available, for example, under the trade names DILATRATE®-SR (Schwarz Pharma, Milwaukee, Wis.); ISORDIL® and ISORDILR TITRADOSE® (Wyeth Laboratories Inc., Philadelphia, Pa.); and SORBITRATE® (Zeneca Pharmaceuticals, Wilmington, Del.). Isosorbide mononitrate is commercially available, for example, under the trade names IMDUR® (A. B. Astra, Sweden); MONOKET® (Schwarz Pharma, Milwaukee, Wis.); and ISMO® (Wyeth-Ayerst company, Philadelphia, Pa.).

"Nitrosated compound" refers to any compound that has been substituted with a nitro group, i.e., —NO$_2$ group. The nitrosated angiotensin-converting enzyme inhibitors, nitrosated beta-adrenergic blockers, nitrosated calcium channel blockers, nitrosated endothelin antagonists, nitrosated angiotensin II receptor antagonists and nitrosated renin inhibitors of the present invention include any known angiotensin-converting enzyme inhibitors, beta-adrenergic blockers, calcium channel blockers, endothelin antagonists, angiotensin II receptor antagonists and renin inhibitors that have been nitrosated through one or more sites such as oxygen (hydroxyl condensation), sulfur (sulfhydryl condensation), and/or nitrogen. The nitrosated compounds of the present invention can be prepared using conventional methods known to one skilled in the art. For example, known methods for nitrosating compounds are described in U.S. Pat. Nos. 5,380,758 and 5,703,073; WO 97/27749; WO 98/19672; and Oae et al, Org. Prep. Proc. Int., 15(3): 165–198 (1983), the disclosures of each of which are incorporated by reference herein in their entirety. WO 98/21193 discloses nitrosated ACE inhibitors and nitrosated beta-adrenergic blockers, the disclosure of which is incorporated by reference herein in its entirety. WO 99/00361 discloses nitrate salts of ACE inhibitors, the disclosure of which is incorporated by reference herein in its entirety.

Suitable angiotensin-converting enzyme inhibitors, include, but are not limited to, alacepril, benazepril, captopril, ceronapril, cilazapril, delapril, duinapril, enalapril, enalaprilat, fosinopril, imidapril, lisinopril, losartan, moveltipril, naphthopidil, pentopril, perindopril, quinapril, ramipril, rentipril, spirapril, temocapril, trandolapril, urapidil, zofenopril, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable beta-adrenergic blockers, include, but are not limited to, acebutolol, alprenolol, amosulalol, arotinolol, atenolol, betaxolol, bethanidine, bevantolol, bisoprolol, bopindolol, bucumolol, bufetolol, bufuralol, bunitrolol, bupranolol, butafilolol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, and the like. Suitable beta-adrenergic blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable calcium channel blockers, include, but are not limited to, amlodipine, aranidipine, barnidipine, benidipine, cilnidipine, clentiazem, diltiazen, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable endothelin antagonists, include, but are not limited to, bosentan, sulfonamide endothelin antagonists, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable angiotensin II receptor antagonists, include, but are not limited to, ciclosidomine, eprosartan, furosemide, irbesartan, losartan, saralasin, valsartan, and the like. Suitable angiotensin II receptor antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable renin inhibitors, include, but are not limited to, enalkrein, RO 42–5892, A 65317, CP 80794, ES 1005, ES 8891, SQ 34017, and the like). Suitable renin inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In the methods of the invention, the antioxidant and at least one compound that donates, transfers or releases nitric oxide, elevates endogenous levels of endothelium-derived relaxing factor, stimulates endogenous synthesis of nitric oxide or is a substrate for nitric oxide synthase, and, optionally, at least one nitrosated compound, and/or compound used to treat cardiovascular diseases can be administered as separate components or as components of the same composition. When the antioxidant and at least one nitric oxide donor are administered as separate components for the treatment of vascular diseases characterized by nitric oxide insufficiency or Raynaud's syndrome, they are preferably administered to the patient at about the same time. "About the same time" means that within about thirty minutes of administering one compound (e.g., antioxidant or nitric oxide donor) to the patient, the other compound (e.g., nitric oxide donor or antioxidant) is administered to the patient. "About the same time" also includes simultaneous administration of the compounds.

In addition to the administration of the combination of the antioxidant and nitric oxide donor for the treatment of vascular diseases characterized by nitric oxide insufficiency, the patients can receive digitalis such as digoxin and/or diuretics and/or at least one nitrosated angiotensin-converting enzyme inhibitor, nitrosated beta-adrenergic blocker, nitrosated calcium channel blocker, nitrosated endothelin antagonist, angiotensin II receptor antagonist, nitrosated renin inhibitor, and/or at least one compound used to treat cardiovascular diseases.

The digoxin is preferably administered orally to achieve a steady state blood serum concentration of at least about 0.7 nanograms per ml to about 2.0 nanograms per ml. The diuretic is administered, preferably orally, to manage edema. Suitable diuretics include, but are not limited to, thiazides (such as, for example, chlorothiazide, hydrochlorothiazide); ethacrynic acid, furosemide, spironalactone, triamterene or mixtures thereof. Depending on the diuretic used, potassium may also be administered to the patient in order to optimize the fluid balance while avoiding hypokalemic alkalosis. The administration of potassium can be potassium chloride or by the daily ingestion of foods with high potassium content such as, for example, bananas, orange juice, and the like. The method of administration of these compounds is described in further detail in U.S. Pat. No. 4,868,179, the disclosure of which is incorporated by reference herein in its entirety.

The compounds and compositions of the invention can be administered by any available and effective delivery system including, but not limited to, orally, bucally, parenterally, by inhalation spray, topically (including transdermally), or rectally in dosage unit formulations containing conventional nontoxic pharmaceutically acceptable carriers, adjuvants, and vehicles as desired. The preferred methods of administration are by oral administration or topical application (transdermal application).

Topical administration can also involve the use of transdermal administration such as transdermal patches or iontophoresis devices. Dosage forms for topical administration of the compounds and compositions can include creams, sprays, lotions, gels, ointments, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

The compositions can also be applied topically using a transdermal system, such as one of an acrylic-based polymer adhesive with a resinous crosslinking agent impregnated with the composition and laminated to an impermeable backing. In a particular embodiment, the compositions of the present invention are administered as a transdermal patch, more particularly as a sustained-release transdermal patch. The transdermal patches of the present invention can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

Solid dosage forms for oral administration can include capsules, sustained-release capsules, tablets, sustained release tablets, chewable tablets, sublingual tablets, effervescent tablets, pills, powders, granules and gels. In such solid dosage forms, the active compounds can be admixed with at least one inert diluent, such as sucrose, lactose or starch. Such dosage forms can also comprise, as is normal practice, additional substances other than inert diluents, e.g., lubricating agents, such as magnesium stearate. In the case of capsules, tablets, effervescent tablets, and pills, the dosage forms can also comprise buffering agents. Soft gelatin capsules can be prepared to contain a mixture of the active compound or composition and vegetable oil. Hard gelatin capsules can contain granules of the active compound in combination with a solid, pulverulent carrier, such as lactose, saccharose, sorbitol, mannitol, potato starch, corn starch, amylopectin, or cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for rectal administration of the compounds or compositions can be prepared by mixing the drug with a suitable nonirritating excipient such as cocoa butter and polyethylene glycols which are solid at room temperature but liquid at rectal temperature, such that they will melt in the rectum and release the drug.

The term parenteral includes subcutaneous injections, intravenous, intramuscular, intrasternal injection, or infusion techniques. Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the invention will typically be administered in a pharmaceutical composition comprising one or more carriers or excipients. Examples of suitable carriers include, for example, water, silicone, waxes, petroleum jelly, polyethylene glycols, propylene glycols, liposomes, sugars, salt solutions, alcohol, vegetable oils, gelatins, lactose, amylose, magnesium stearate, talc, surfactants, silicic acids, viscous paraffins, perfume oils, fatty acid monoglycerides and diglycerides, petroethral fatty acid esters, hydroxymethylcelluloses, polyvinyl-pyrrolidones, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds. For topical application, the compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacycoheptan-2-ones (available under the trademark AZONE from Nelson Research & Development Co., Irvine Calif.), alcohols and the like. For parenteral application, particularly suitable vehicles consist of solutions, preferably oily or aqueous solutions, as well as suspensions, emulsions, or implants. Aqueous suspensions can contain substances which increase the viscosity of the suspension and include, for example, sodium carboxymethyl cellulose, sorbitol and/or dextran. Optionally, the suspension can contain stabilizers. The compositions, if desired, can also contain minor amounts of wetting agents, emulsifying agents and/or pH buffering agents.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules, nanoparticles, and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the present invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Particular sustained release dosage forms of the present invention comprise biodegradable microparticles or nanoparticles. More particularly, biodegradable microparticles or nanoparticles are formed of a polymer containing matrix that biodegrades by random, nonenzymatic, hydrolytic scissioning to release therapeutic agent, thereby forming pores within the particulate structure.

In a particular embodiment, the compositions of the present invention are orally administered as a sustained release tablet or a sustained release capsule. For example, the sustained release formulations can comprise a therapeutically effective amount of at least one antioxidant or a pharmaceutically acceptable salt thereof, and at least one nitric oxide donor, or the sustained release formulations can comprise a therapeutically effective amount of at least one antioxidant or a pharmaceutically acceptable salt thereof, and at least one nitric oxide donor, and, optionally at least one nitrosated compound. In a particular embodiment the sustain release formulation comprises hydralazine hydrochloride and isosorbide dinitrate and/or isosorbide mononitrate.

While individual needs may vary, determination of optimal ranges for effective amounts of the compounds and/or compositions is within the skill of the art and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

In particular embodiments, the hydralazine hydrochloride can be administered in an amount of about 30 milligrams per day to about 400 milligrams per day; the isosorbide dinitrate can be administered in an amount of about 5 milligrams per day to about 200 milligrams per day; and the isosorbide mononitrate can be administered in an amount of about 5 milligrams per day to about 120 milligrams per day. In a more particular embodiment, the hydralazine hydrochloride can be administered in an amount of about 50 milligrams per day to about 300 milligrams per day; the isosorbide dinitrate can be administered in an amount of about 20 milligrams per day to about 160 milligrams per day; and the isosorbide mononitrate can be administered in an amount of about 15 milligrams per day to about 100 milligrams per day. In an even more particular embodiment, the hydralazine hydrochloride can be administered in an amount of about 75 milligrams one to four times per day; the isosorbide dinitrate can be administered in an amount of about 40 milligrams one to four time per day; and the isosorbide mononitrate can be administered in an amount of about 20 milligrams one to four times per day. The particular amounts of hydralazine and/or isosorbide dinitrate or isosorbide mononitrate can be administered as a single dose once a day; or in multiple doses several times throughout the day; or as a sustained-release oral formulation; or as a transdermal sustained release patch.

The dose of nitric oxide donor in the composition will be dependent on the specific nitric oxide donor compound and the mode of administration. For example, when L-arginine is the orally administered nitric oxide donor, it can be administered in an amount of about 3 grams to about 15 grams to provide a plasma level in the range of about 0.2 mM to about 30 mM.

The present invention also provides pharmaceutical kits comprising one or more containers filled with one or more of the ingredients of the pharmaceutical compounds and/or compositions. Such kits can also include, for example, other compounds and/or compositions (e.g., diuretics, digoxin, nitrosated compounds, compounds used to treat cardiovascular diseases and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following examples are for purposes of illustration only, and are not intended to limit the scope of the specification or claims.

Example 1

Figure 2:
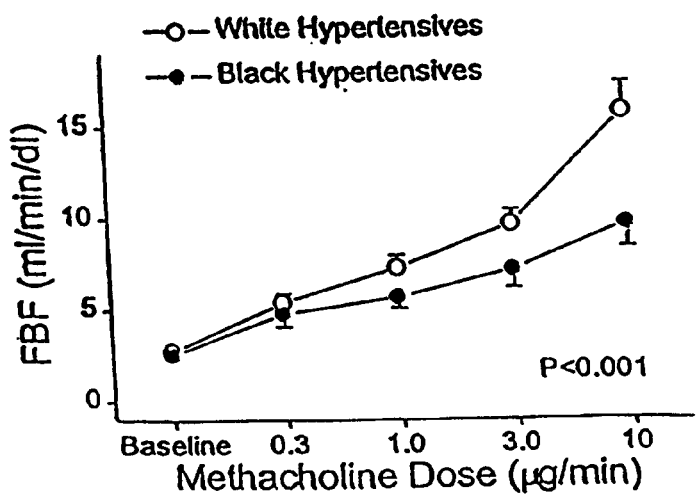
FIG. 2 shows forearm blood flow responses to intra-arterial methacholine that were assessed using venous occlusion plethysmography in 20 white and 16 black patients with a clinical history of hypertension (BP>140/90).

As described herein, NO deficiency is a central pathophysiologic mechanism for the black vascular diathesis. To examine this issue in forearm microvessels, the vasodilator responses to intra-arterial infusions of methacholine, sodium nitroprusside, and verapamil were examined using venous occlusion plethysmography in 36 white and black hypertensive patients. These patients had no other coronary factors, such as smoking, diabetes mellitus, or hypercholesterolemia, and the two groups were matched in terms of age, gender, lipid levels, blood pressure, and anti-hypertensive treatment. Similar to previous reports (Lang et al, *N Engl J Med*, 333:155–160 (1995); Panza et al, *N Engl J Med*, 323:22–27 (1990)), the dilator response to methacholine, but not nitroprusside, was significantly reduced in these hypertensive patients compared to age-matched normotensive controls (Sherman et al, *Circulation*, 98:1–376 (1998)). Regarding racial differences, as shown in FIG. 2, vasodilation in response to methacholine was markedly worse in the black hypertensive patients compared to white hypertensive patients. There were no racial differences in the responses to sodium nitroprusside or verapamil (data not shown), suggesting that this impairment of NO action in black hypertensives is at the endothelial level and that dysfunction of vascular smooth muscle does not account for the impaired response. These findings have important implications for the pathogenesis of hypertension and myocardial ischemia.

Example 2

Figure 3A:
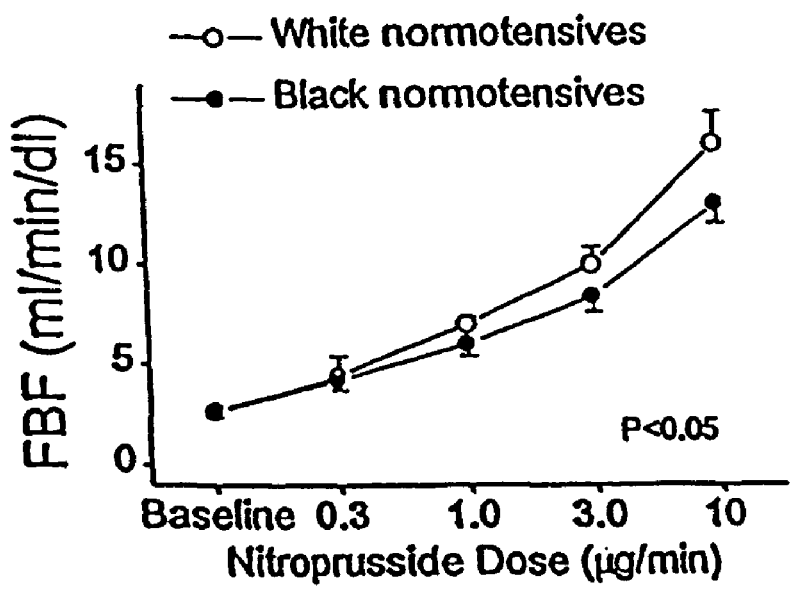
FIGS. 3A and 3B show forearm blood flow responses to nitroprusside (FIG. 3A) and methacholine (FIG. 3B) that were assessed by venous occlusion plethysmography in 25 white and 21 black patients without hypertension. The dilator response to sodium nitroprusside (FIG. 3A) was significantly lower in black patients, while there was no racial difference in response to methacholine (FIG. 3B).
Figure 3B:
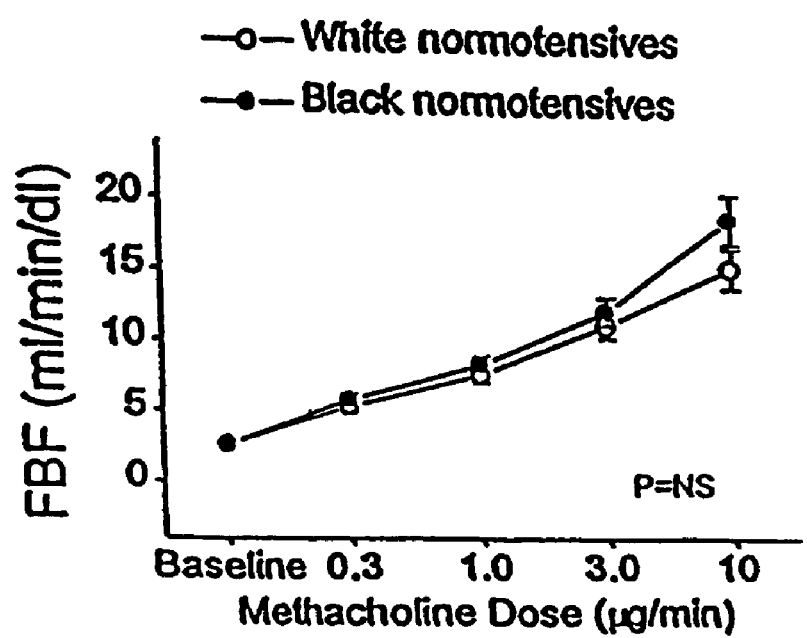

To investigate the issue of whether NO deficiency is a primary or secondary phenomenon in hypertensive black patients, 46 normotensive white and black patients who were matched for age and gender were compared. As shown in FIG. 3B, the vasodilator responses to methacholine were not significantly different in black and white normotensive patients. However, the response to sodium nitroprusside (FIG. 3A) was significantly lower in the black normotensive patients. This finding shows that there is an impairment in the vasodilator response exogenous source of NO in black patients even prior to the development of hypertension, an observation that would be consistent with a primary rather than secondary role in the black vascular diathesis. These findings are consistent with recently published results by other investigators (Lang et al, *N Engl J Med*, 333:155–160 (1995); Cardillo et al, *Hypertension* 31:1235–1239 (1998)).

Example 3

Figure 4A:
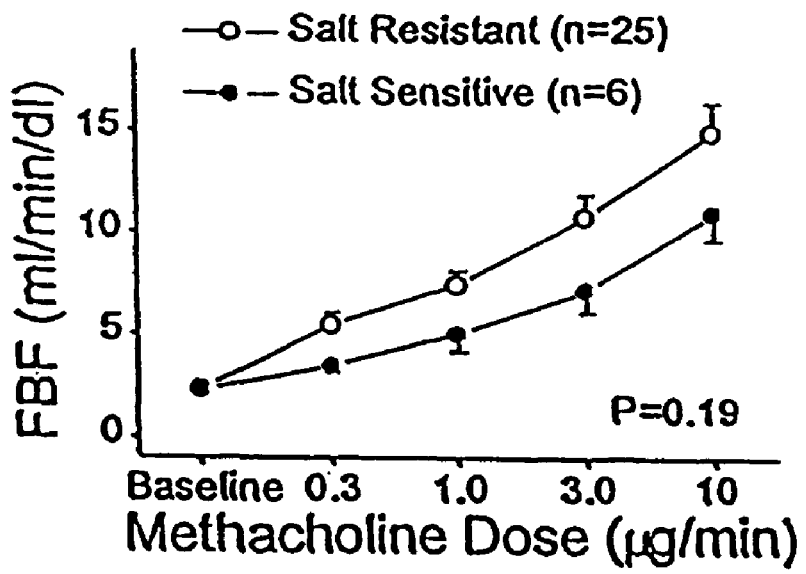
FIGS. 4A and 4B show the effect of salt-sensitivity on forearm microvascular function. By repeated measures ANOVA, there were trends for impaired responses to methacholine (FIG. 4A) and sodium nitroprusside (FIG. 4B) in salt-sensitive black patients.
Figure 4B:
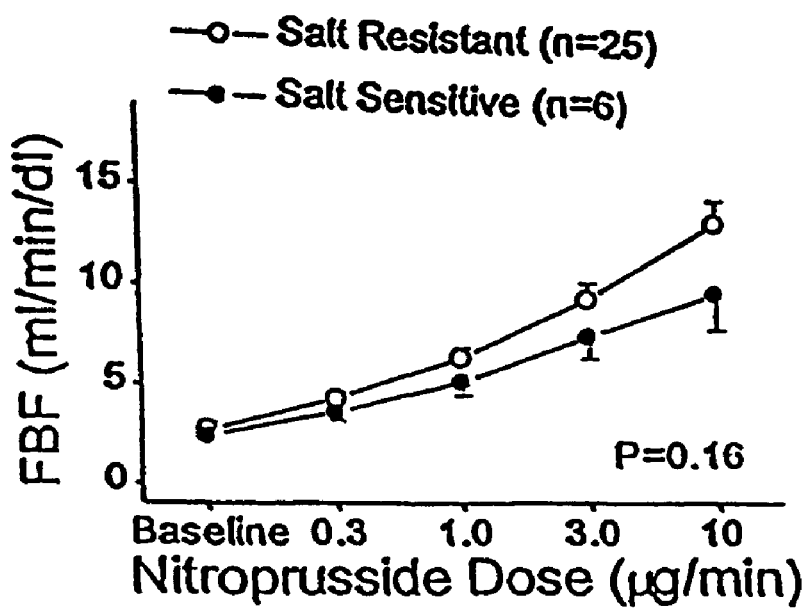

Black patients have a preponderance of salt-sensitive hypertension, and the data described herein show that NO deficiency is a pathogenic mechanism of salt-sensitive hypertension in experimental models (Rudd et al, *Am J Physiol*, 277: H732–H739 (1999)). To explore the relation between salt-sensitivity and endothelium-derived NO action in black patients prior to the development of hypertension, the blood pressure response to salt-loading and salt-deprivation using an established inpatient protocol (Weinberger et al, *Hypertension*, 8:II-127–II-134 (1986)) in a group of normotensive black patients was assessed. Briefly, blood pressure was continuously monitored non-invasively during a salt load (sodium 458 mEq over 24 hours) and during a period of salt depletion (furosemide treatment and sodium intake 10 mEq over 24 hours). Patients were considered to be salt-sensitive if mean blood pressure was at least 10 mm Hg higher during the salt loading period (Weinberger et al, *Hypertension*, 8:II-127–II-134 (1986)). As shown in FIGS. 4A-B, there were trends for impaired vasodilator responses to both methacholine (FIG. 4A) and sodium nitroprusside (FIG. 4B). The vasodilator responses to verapamil were equivalent in salt-sensitive and salt-resistant patients (data not shown). These data show impaired NO action in the microvasculature of salt sensitive individuals prior to the development of hypertension.

Example 4

The effects of hypertension and race on conduit vessel function were examined using a well-established brachial ultrasound technique (Vita et al, Lanzer & Lipton, Eds., *Diagnostics of Vascular Diseases: Principles and Technology*. Berlin:Springer-Verlag, pp.249–259 (1996)) in 370 patients (178 black, 192 white). As shown in Table 1, there were no significant differences in flow-mediated dilation or nitroglycerin-mediated dilation according to race. However, hypertension was associated with a highly significant reduction in both flow-mediated dilation and nitroglycerin-mediated dilation. Further, systolic blood pressure was inversely correlated with flow-mediated dilation (r=−0.30, P<0.001) and nitroglycerin-mediated dilation (r=−0.33, P<0.001). Diastolic pressure correlated to a similar extent with vascular function. By multiple linear regression analysis, vessel size and systolic blood pressure were the only independent predictors of flow-mediated dilation in this sizable group of patients. Thus, both black and white patients with hypertension demonstrate a significant impairment of NO action in conduit arteries (Gokce et al, *Circulation*, 99(25) 3234–3240 (1999)).

TABLE 1

Conduit Vasomotor Function By Race

|  | White Patients | Black Patients | P |
|---|---|---|---|
| FMD (%) | | | |
| Normotensive | 11.5 ± 5.9 | 13.3 ± 7.2 | NS |
| Hypertensive | 9.5 ± 5.3* | 8.8 ± 6.2* | NS |
| NTG-response (%) | | | |
| Normotensive | 18.1 ± 8.1 | 20.6 ± 8.4 | NS |
| Hypertensive | 14.6 ± 6.2* | 16.4 ± 7.1* | NS |

Data are mean ± SD.
*p < 0.001 compared to race matched normotensives.

Each of the above examples demonstrate that NO action is impaired in the microvasculature of black hypertensive patients to a greater extent than in white hypertensive patients. There is a suggestion that this abnormality may precede the development of hypertension, particularly in salt-sensitive individuals, consistent with a pathogenic role. In conduit vessels, a marked impairment of NO action that may contribute to ischemic heart disease and stroke has been demonstrated. This abnormality appears to be independent of race, a finding that is consistent with possibility that the impairment is a consequence of blood pressure elevation of any cause. Since African Americans have a greater incidence of hypertension and a preponderance of salt-sensitive hypertension, these findings lend further support to the hypothesis that nitric oxide insufficiency contributes to the pathogenesis of ischemic heart disease in this population.

The disclosure of each patent, patent application and publication cited herein is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A method to treat a vascular disease resulting from nitric oxide insufficiency in a patient comprising administering to the patient a therapeutically effective amount of at least one antioxidant enzyme, and at least one compound that donates, transfers, or releases nitric oxide, or induces the production of endogenous nitric oxide, or endothelium-derived relaxing factor, or is a substrate for nitric oxide synthase, or a pharmaceutically acceptable salt thereof, wherein the antioxidant enzyme is superoxide dismutase, catalase, glutathione peroxidase, or a mixture thereof and the vascular disease resulting from nitric oxide insufficiency is a disease resulting from oxidative stress and wherein the at least one antioxidant enzyme, and the at least one compound that donates, transfers, or releases nitric oxide, or induces the production of endogenous nitric oxide, or endothelium-derived relaxing factor, or is a substrate for nitric oxide synthase are administered as components of the same composition, or are administered as separate components at about the same time.

2. The method of claim 1, further comprising administering a pharmaceutically acceptable carrier.

3. The method of claim 1, wherein the said at least one compound that donates, transfers, or releases nitric oxide, or induces the production of endogenous nitric oxide, or endothelium-derived relaxing factor, or is a substrate for nitric oxide synthase is selected from the group consisting of S-nitroso-N-acetylpenicillamine, S-nitroso-homocysteine, S-nitroso-cysteine, S-nitroso-glutathione and S-nitroso-cysteinyl-glycine.

4. The method of claim 1, wherein the at least one compound that donates, transfers, or releases nitric oxide, or induces the production of endogenous nitric oxide, or endothelium-derive relaxing factors, or is a substrate for nitric oxide synthase is selected from the group consisting of L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine; and lysine.

5. The method of claim 1, wherein the at least one antioxidant enzyme and the at least one compound that donates, transfers, or releases nitric oxide, or induces the production of endogenous nitric oxides, or endothelium-derived relaxing factor, or is a substrate for nitric oxide synthase, or a pharmaceutically acceptable salt thereof are administered orally, or parenterally.

6. The method of claim 5, wherein the at least one antioxidant enzyme and the at least one compound that donates, transfers, or releases nitric oxide, or induces the production of endogenous nitric oxide, or endothelium-derived relaxing factor, or is a substrate for nitric oxide synthase, or a pharmaceutically acceptable salt thereof are administered orally.

7. The method of claim 6, wherein the at least one antioxidant enzyme and the at least one compound that donates, transfers, or releases nitric oxide, or induces the production of endogenous nitric oxide, or endothelium-derived relaxing factor, or is a substrate for nitric oxide synthase, or a pharmaceutically acceptable salt thereof are administered orally as a solid dose, a liquid dose or a suspension.

8. The method of claim 7, wherein the solid dose is a tablet or capsule.

9. The method of claim 7, wherein the solid dose is a sustained release capsule or a sustained release tablet.

10. The method of claim 8, wherein the tablet or capsule is a sublingual tablet or a sublingual capsule.

11. The method of claim 8, wherein the tablet or capsule is a chewable tablet or a chewable capsule.

12. The method of claim 1, further comprising administering a therapeutically effective edema managing amount of a diuretic compound.

13. The method of claim 12, wherein the diuretic compound is a thiazide, ethacrynic acid, a furosemide, a spiranolactone, a triamterene, or a mixture thereof.

14. The method of claim 12, further comprising administering a therapeutically effective amount of potassium.

15. The method of claim 14, wherein the potassium is administered as potassium chloride or by the daily ingestion of foods with high potassium content.

16. The method of claim 1, further comprising administering at least one nitrosated angiotensin-converting enzyme inhibitor, nitrosated beta-adrenergic blocker, nitrosated calcium channel blocker, nitrosated endothelin antagonist, nitrosated angiotensin II receptor antagonist, nitrosated renin inhibitor, or a mixture thereof.

17. The method of claim 1, wherein the at least one compound that donates, transfers, or releases nitric oxide, or induces the production of endogenous nitric oxide or endothelium-derived relaxing factor or is a substrate for nitric oxide synthase is isosorbide dinitrate and/or isosorbide mononitrate.

* * * * *